United States Patent [19]

Sullivan

[11] 4,112,925
[45] Sep. 12, 1978

[54] BLOOD SAMPLE CONTAINER HAVING AN ANTICOAGULANT COATING OF POLYVINYL PYRROLIDONE AND A SALT OF ETHYLENE DIAMINE TETRACETATE

[75] Inventor: Kevin J. Sullivan, Painted Post, N.Y.

[73] Assignee: Corning Glass Works, Corning, N.Y.

[21] Appl. No.: 805,525

[22] Filed: Jun. 10, 1977

Related U.S. Application Data

[62] Division of Ser. No. 679,166, Apr. 22, 1976, Pat. No. 4,069,185.

[51] Int. Cl.$^2$ .............................................. A61B 5/00
[52] U.S. Cl. ........................... 128/2 F; 260/29.6 HN; 260/29.6 N; 260/29.6 E
[58] Field of Search ............... 128/2 F; 260/29.6 HN, 260/29.6 N, 29.6 E; 526/264

[56] References Cited

U.S. PATENT DOCUMENTS

| 3,288,707 | 11/1966 | Hurwitz et al. | 260/29.6 HN |
|---|---|---|---|
| 3,527,719 | 9/1970 | Hurwitz et al. | 260/29.6 HN |
| 3,554,287 | 1/1971 | Eilers et al. | 260/29.6 HN |
| 3,926,564 | 12/1975 | Giaever | 128/2 G |
| 4,057,052 | 11/1977 | Kaufman et al. | 128/2 F |
| 4,066,067 | 1/1978 | Micheli | 128/2 F |

Primary Examiner—M. J. Welsh
Attorney, Agent, or Firm—Walter S. Zebrowski; Clarence R. Patty, Jr.

[57] ABSTRACT

An anticoagulant coating composition suitable for coating the interior surfaces of a blood microsample collection tube, such as a capillary tube, is disclosed. The coating composition consists essentially of ethylene diamine tetracetate held in a matrix of polyvinyl pyrrolidone. Both the ethylene diamine tetracetate and the polyvinyl pyrrolidone are dissolved in a water-alcohol mixture to form a coating composition solution.

1 Claim, No Drawings

BLOOD SAMPLE CONTAINER HAVING AN ANTICOAGULANT COATING OF POLYVINYL PYRROLIDONE AND A SALT OF ETHYLENE DIAMINE TETRACETATE

CROSS-REFERENCE TO RELATED APPLICATION

This is a division of application Ser. No. 679,166 filed Apr. 22, 1976, now U.S. Pat. No. 4,069,185.

BACKGROUND OF THE INVENTION

Although ethylene diamine tetracetate (EDTA) has been known in the prior art as an anticoagulant for use in the collection of blood samples, its normal use has heretofore been limited to the partially evacuated tubes used for collecting relatively large blood samples, such as 2 ml or more for example, from the hypodermic puncture of a patient's vein.

It is often not practical nor advisable to perform a venipuncture in certain medical cases, such for example as pediatrics, geriatrics, severe burns, and the like. In such cases, a "micro" sample of blood is obtained from a superficial skin puncture of the fingertip, heel, or earlobe. A typical "micro" sample volume of 250 $\mu$l is obtained using this procedure. The specimen is collected directly from a blood droplet on the skin surface into a glass micro-pipette. If an anticoagulant is not mixed into the blood sample, it will clot within a few minutes.

Prior art blood microsample collection tubes have been coated on the inner walls with a small amount of the anticoagulant heparin, typically in amounts of 25 $\mu$g in a 250 $\mu$l tube. However, heparinized blood has staining characteristics which make it unsuitable for microscopic examination. Ethylene diamine tetracetate is the anticoagulant of choice for tests involving microscopic examination since it preserves cellular morphology fairly well and does not introduce any staining artifacts. However, ethylene diamine tetracetate has a relatively high minimum effective concentration, typically 250 $\mu$g in a 250 $\mu$l sample tube. This factor alone has seriously hindered previous attempts to produce ethylene diamine tetracetate coated microsample tubes although other serious problems included poor adhesion of the dry ethylene diamine tetracetate to the glass tube walls, as well as poor mixing of the dry EDTA with the blood sample, resulting in the formation of small clots.

SUMMARY OF THE INVENTION

The objects of the present invention are to provide an anticoagulant coating composition suitable for coating capillary tubes or other containers used to collect blood microsamples for hematologic examination, which coating composition must be physically and chemically stable, and readily soluble in the blood specimen. The anticoagulant must not deform the cellular elements in the blood, or disturb the staining characteristics of these cells.

Additional objects of this invention are to provide an anticoagulant coating composition that uniformly covers the inner walls of a collection tube, does not inhibit fluid flow by capillary action, and overcomes the heretofore noted disadvantages.

Broadly, according to the present invention, an anticoagulant coating composition suitable for applying to the interior surfaces of blood microsample collection tubes or other containers is provided having from about 5 percent to about 95 percent by weight ethylene diamine tetracetate held in a matrix of polyvinyl pyrrolidone, which reagents are dissolved in a water-alcohol mixture.

Additional objects, features, and advantages of the present invention will become apparent to those skilled in the art from the following detailed description in which by way of example, only the preferred embodiments of this invention are illustrated.

DETAILED DESCRIPTION

The anticoagulant coating composition of the present invention is suitable for coating capillary tubes or other containers for blood microscope collection, such as those described in my copending U.S. patent application entitled "Fluid Application Device," Ser. No. 598,590, filed July 24, 1975, which application is hereby expressly incorporated herein by reference.

The anticoagulant coating composition of the present invention consists essentially of a suspension of a salt of ethylene diamine tetracetate anticoagulant in a matrix of polyvinyl pyrrolidone, a water soluble polymer. As a means of applying the anticoagulant coating, these reagents are dissolved in a water-alcohol solvent. This mixture provides good adhesion of the anticoagulant to the walls of the sample tube while facilitating rapid dissolution of the anticoagulant into the blood sample. As will be understood, various salts of ethylene diamine tetracetate exist and are suitable for the purposes of the present invention although tripotassium EDTA is preferred.

As a typical example of the present invention, an anticoagulant coating composition was prepared by dissolving 2.5 grams of tripotassium ethylene diamine tetracetate and 10 grams of polyvinyl pyrrolidone in 100 ml of a solvent comprising by volume 50 percent methyl alcohol and 50 percent water. A volume of 10 $\mu$l of this solution was then dispensed into one end of a "Natelson" type blood microsample collection tube having an outside diameter of 3.0 mm, an inside diameter of 1.5 mm and a volume of about 265 $\mu$l. This quantity of coating solution was then allowed to flow down the tube leaving a uniform coating on the inner wall. As it passed down the tube, the quantity reduced in volume, being fully dissipated just before reaching the bottom of the tube. This coating was then dried in situ by placing the tube in a flowing warm air oven for 2 hours at 85° C. After the solvents evaporated, the remaining anticoagulant coating consisted of 250 $\mu$g of ethylene diamine tetracetate suspended in a matrix of 1 mg of polyvinyl pyrrolidone.

As an experimental control, tubes were also coated with 250 $\mu$g of ethylene diamine tetracetate only, using the technique described above. The two types of tubes coated with ethylene diamine tetracetate in a matrix of polyvinyl pyrrolidone and ethylene diamine tetracetate only were then used to collect blood microsamples from fingertip punctures. Using standard techniques, blood was collected directly from blood droplets on the skin surface, the sample flowing into the tube through the forces of gravity and capillary action. It was noted that capillary action was significantly inhibited in the tubes coated with ethylene diamine tetracetate alone, making them difficult to fill while the tubes coated with ethylene diamine tetracetate in a matrix of polyvinyl pyrrolidone exhibited good capillary action.

After filling, each tube was rocked to mix the blood with the anticoagulant, sealed, and stored in a vertical position. After two hours, the tubes were opened and rocked to remix the blood specimen. The blood was then used to produce standard blood smears which were subsequently stained with a Wright-Giesma stain using standard techniques. It was noted that some of the blood specimens stored in tubes coated with ethylene diamine tetracetate only contained small clots, with an occasional tube clotted to such an extent that the blood could not be drained therefrom. The tubes coated with ethylene diamine tetracetate in a matrix of polyvinyl pyrrolidone exhibited no clotting; and upon microscopic examination, the smears prepared from these tubes showed excellent preservation of cellular morphology and good staining characteristics.

Although the reasons are not known, it is theorized that the problems encountered with the tubes coated with EDTA alone are due to slow dissolution of the EDTA into the blood specimen. The hygroscopic nature of the polyvinyl pyrrolidone matrix maintains the EDTA in a "predissolved" state, which facilitates its rapid mixing with the blood specimen. These mixing problems are more prevalent in capillary sampling tubes than in larger blood sample tubes because glass is an activator of the clotting reaction and the small blood sample in a capillary tube is exposed to a much higher proportion of glass surface area.

Table I, following, sets out various other examples of the anticoagulant coating solution of the present invention.

Table I

| SOLUTE CONCENTRATION | | SOLVENT COMPOSITION | |
| --- | --- | --- | --- |
| Salt of Ethylene Diamine Tetracetate g/100 ml | Polyvinyl Pyrrolidene g/100 ml | Water Percent by Volume | Methanol Percent by Volume |
| 1 | 10 | 10 | 90 |
| 1 | 10 | 0 | 100 |
| 2.5 | 1.5 | 10 | 90 |
| 2.5 | 2.5 | 10 | 90 |
| 2.5 | 2.5 | 25 | 75 |
| 4 | 2 | 25 | 75 |
| 4 | 3 | 100 | 0 |
| 10 | 0.5 | 25 | 75 |
| 10 | 0.5 | 50 | 50 |
| 10 | 1 | 25 | 75 |
| 10 | 1 | 50 | 50 |
| 10 | 2 | 20 | 80 |
| 10 | 2 | 25 | 75 |
| 10 | 2 | 33 | 67 |
| 10 | 2 | 40 | 60 |
| 10 | 2 | 50 | 50 |
| 10 | 2 | 67 | 33 |
| 10 | 2 | 80 | 20 |
| 10 | 5 | 50 | 50 |
| 12 | 2 | 30 | 70 |
| 16 | 9 | 55 | 45 |
| 23 | 4 | 56 | 44 |

As is understood, the anticoagulant coating solution of the present invention comprises a solvent and solid constituents, herein referred to as the filler, namely a salt of ethylene diamine tetracetate and polyvinyl pyrrolidone. The solvent plays no direct role in the anticoagulant action of the tube coating, since it is evaporated during the final step of the coating process. The composition of the solvent is chosen to facilitate the coating process.

Ethylene diamine tetracetate is readily soluble in water while polyvinyl pyrrolidone is soluble in water and many polar organic solvents, such for example as methanol, ethanol, isopropanol, alcohols, or the like. A usable coating solution can be produced with an ethylene diamine tetracetate-polyvinyl pyrrolidone-water solution, however, it has been found that a coating solution based on a mixed alcohol-water solvent gives a more uniform coating action and is more readily evaporated from the tube after coating. Methanol is preferred as the alcohol due to its economy and high volatility. The best coatings are obtained with high methanol-water ratios. Such ratios are limited by the solubility of EDTA, which is a complicated function of the relative concentrations of water, methanol and polyvinyl pyrrolidone. A solvent of 90 percent methanol and 10 percent water is particularly suitable; this being the minimum amount of water that will hold ethylene diamine tetracetate in solution at a concentration of 2.5 g/100 ml in the presence of polyvinyl pyrrolidone at a concentration of 2.5 g/100 ml. Of course, at other EDTA or polyvinyl pyrrolidone concentrations, this limiting methanol-water ratio will change as will be understood in the art.

The primary function of polyvinyl pyrrolidone in the tube coating is as a matrix to hold a salt of ethylene diamine tetracetate on the walls of the sample tube, and to facilitate the rapid dissolution of the ethylene diamine tetracetate into the blood sample. It has the secondary beneficial effect of helping maintain cellular morphology during the staining of the smear made from the blood sample.

It has been found that usable coatings with polyvinyl pyrrolidone concentrations ranging from 5 percent to 90 percent of the dried coating weight are suitable for the present invention. At lower polyvinyl pyrrolidone concentrations, the coating becomes unusable because of poor capillary action in the coated tubes and occasional small clots in the blood sample due to slow dissolution. The high limit on polyvinyl pyrrolidone concentration is imposed by its limited solubility in the coating solution solvent. The optimal choice of polyvinyl pyrrolidone concentration involves considerations of coating uniformity and capillary action in the coated tube. It has been found that final dried coating compositions in the range of about 50 percent of a salt of ethylene diamine tetracetate and 50 percent polyvinyl pyrrolidone give best all around performance.

It has been found that usable coatings with salt of ethylene diamine tetracetate concentrations ranging from 10 percent to 95 percent of the dried coating weight are suitable for the present invention. As will be understood, this parameter is fixed by the volume of coating solution used per tube, and by the desired final ethylene diamine tetracetate content per tube. An acceptable dosage for "in vitro" anticoagulation by EDTA is generally about 1 mg/ml of blood. Accordingly, 250 µg of EDTA in a 250 µl collection tube would be required. As will also be understood, this concentration may be varied to accommodate predetermined desired results.

Although the present invention has been described with respect to details of certain embodiments thereof, it is not intended that such details be limitations upon the scope of the invention except insofar as set forth in the following claims.

I claim:
1. A blood sample container comprising
   a capillary tube, and
   an anticoagulant coating applied to the interior surface of said capillary tube consisting essentially of from about 10 percent to about 95 percent by weight of a salt of ethylene diamine tetracetate, and from about 5 percent to about 90 percent by weight of polyvinyl pyrrolidone.

* * * * *